United States Patent
Lee et al.

(10) Patent No.: US 11,550,393 B1
(45) Date of Patent: Jan. 10, 2023

(54) META VERSE MULTIMEDIA SYSTEM BASED ON BRAINWAVES

(71) Applicants: Ching Lee, Taipei (TW); Ruey Yuan Lee, Taipei (TW)

(72) Inventors: Ching Lee, Taipei (TW); Ruey Yuan Lee, Taipei (TW)

(73) Assignees: Ching Lee, Taipei (TW); Ruey Yuan Lee, Taipei (TW)

( * ) Notice: Subject to any disclaimer, the term of this patent is extended or adjusted under 35 U.S.C. 154(b) by 0 days.

(21) Appl. No.: 17/853,962

(22) Filed: Jun. 30, 2022

(51) Int. Cl.
 *G06F 3/01* (2006.01)
 *A61B 5/00* (2006.01)
 *A61B 5/374* (2021.01)

(52) U.S. Cl.
 CPC ............. *G06F 3/015* (2013.01); *A61B 5/374* (2021.01); *A61B 5/6814* (2013.01); *G06F 2203/011* (2013.01)

(58) Field of Classification Search
 CPC . G06F 3/015; G06F 2203/011; A61B 5/6814; A61B 5/374
 USPC ........................................................ 345/156
 See application file for complete search history.

(56) References Cited

U.S. PATENT DOCUMENTS

| | | | | |
|---|---|---|---|---|
| 2018/0071648 | A1* | 3/2018 | Chhatlani | A63H 27/12 |
| 2019/0201691 | A1* | 7/2019 | Poltorak | A61M 21/00 |
| 2019/0247662 | A1* | 8/2019 | Poltroak | A61B 5/0816 |
| 2019/0307350 | A1* | 10/2019 | Sridhar | A61B 5/6803 |

* cited by examiner

*Primary Examiner* — Calvin C Ma

(57) ABSTRACT

A metaverse multimedia system based on user brainwaves causes that emotional messages, voice messages and color messages could be captured from the brainwaves of the users. The emotional messages are integrated to the role of the user in the metaverse space. Hence, the role in the metaverse can respond the emotions of the user, while the voice messages and color messages are integrated into the sceneries in the metaverse, which is selected by the user. As a result, the metaverse space completely presents user's states of mind which are captured from the brainwaves of the users. Furthermore the whole sceneries and presentations of the roles in the metaverse space are adjustable with the changes of the users. It can also express user's personalities. Interaction modes between the users and visitors entering into the metaverse space of the user could be analyzed based on the method disclosed in the present invention.

15 Claims, 5 Drawing Sheets

META VERSE MULTIMEDIA SYSTEM BASED ON BRAINWAVES

FIELD OF THE INVENTION

The present invention is related to brainwaves and metaverse, and in particular to a metaverse multimedia system based on brainwaves,

BACKGROUND OF THE INVENTION

Currently, from the research of brainwaves, it is knows that the tightness, hearing ability, memory, logical ability, visual ability, reaction can be acquired from analysis of brainwaves. The brainwaves of human mainly include Delta wave, Theta waves, High/Low Alpha waves, High/Low Beta waves and High/Low Gamma waves of the left and right brains of the testers. These brainwaves have different physical, physiological, and psychological meanings, which expresses different conditions of the testers. Therefore, by measuring brainwaves and numerical operations thereto, characters and emotions of the users can be got. These have been widely and deeply researched academically. The operations are executed in relative semiconductor chips.

Recently, concept of Metaverse is abruptly popular all over the world. One of the important features in Metaverse is how to imitate the human characters so as to make the virtual world more approaches the real world. It is known that Helmet brainwaves detectors can get the states of the brainwaves real time. By serial tests about emotions, reactions, and preference to find characters of human is a big trend in research of brainwaves. For example, Theta waves and Low Alpha waves are helpful to find the creations and inspiration of humans.

Therefore, since inventors of the present invention have worked in this field for many years and owns plentiful professional knowledge about these fields, they desire to propose a novel method which combines characters of brainwaves and digital coding systems so as to resolve problems encountered in the prior art.

SUMMARY OF THE INVENTION

Accordingly, the object of the present invention is to provide a metaverse multimedia system based on brainwaves, wherein emotional messages, voice messages and color messages are captured from the brainwaves of the users. The emotional messages are integrated to the role of the user in the metaverse space. Hence, the role in the metaverse can respond the emotions of the user, while the voice messages and color messages are integrated into the sceneries in the metaverse, which is selected by the user. As a result, the metaverse space completely presents user's states of mind which are captured from the brainwaves of the users. Furthermore the whole sceneries and presentations of the roles in the metaverse space are adjustable with the changes of the users. It can also express user's personalities. Further, interaction modes between the users and visitors entering into the metaverse space of the user could be analyzed based on the method disclosed in the present invention. Therefore, the present invention cause that a social media could present a virtual reality which is lifelike and closer to the real life as the user live in a real world.

To achieve above object, the present invention provides a metaverse multimedia system based on brainwaves, comprising: a helmet for detecting brainwaves of a user; the helmet including a ring, a brainwave detector on the ring for detecting brainwaves, and a detector transceiver connected to the brainwave detector for transmitting the brainwaves from the brainwave detector; a processing unit connected to the helmet receiving the brainwave signals from the helmet and processing the signals; these brainwave signals including signals of brainwaves from the left brain and right brain of the user, which contains Delta wave, Theta waves, High/Low Alpha waves, High/Low Beta waves and High/Low Gamma waves; and the processor including: a processor end transceiver connected to the detector transceiver for receiving signals from the brainwave transceiver; a melody convertor connected to the processing end transceiver for converting the brainwave signals of the user into respective music melodies by a specific algorithm; a color convertor connected to the processing end transceiver for converting brainwave signals of the user into specific colors according to specific algorithms; a scenery database storing various sceneries which are selected by the users as a background space for presenting in a metaverse; and a scenery player connected to the scenery database for displaying the music and melodies from the melody convertor; color messages from the color convertor, and the sceneries outputted from the scenery database; the states of the sceneries changes based on the outputted from the melody convertor and the color convertor.

DETAILED DESCRIPTION OF THE INVENTION

In order that those skilled in the art can further understand the present invention, a description will be provided in the following in details.

However, these descriptions and the appended drawings are only used to cause those skilled in the art to understand the objects, features, and characteristics of the present invention, but not to be used to confine the scope and spirit of the present invention defined in the appended claims.

Referring to FIGS. 1 to 4, the structure of the present invention is illustrated. The present invention includes the following elements.

Figure 1:
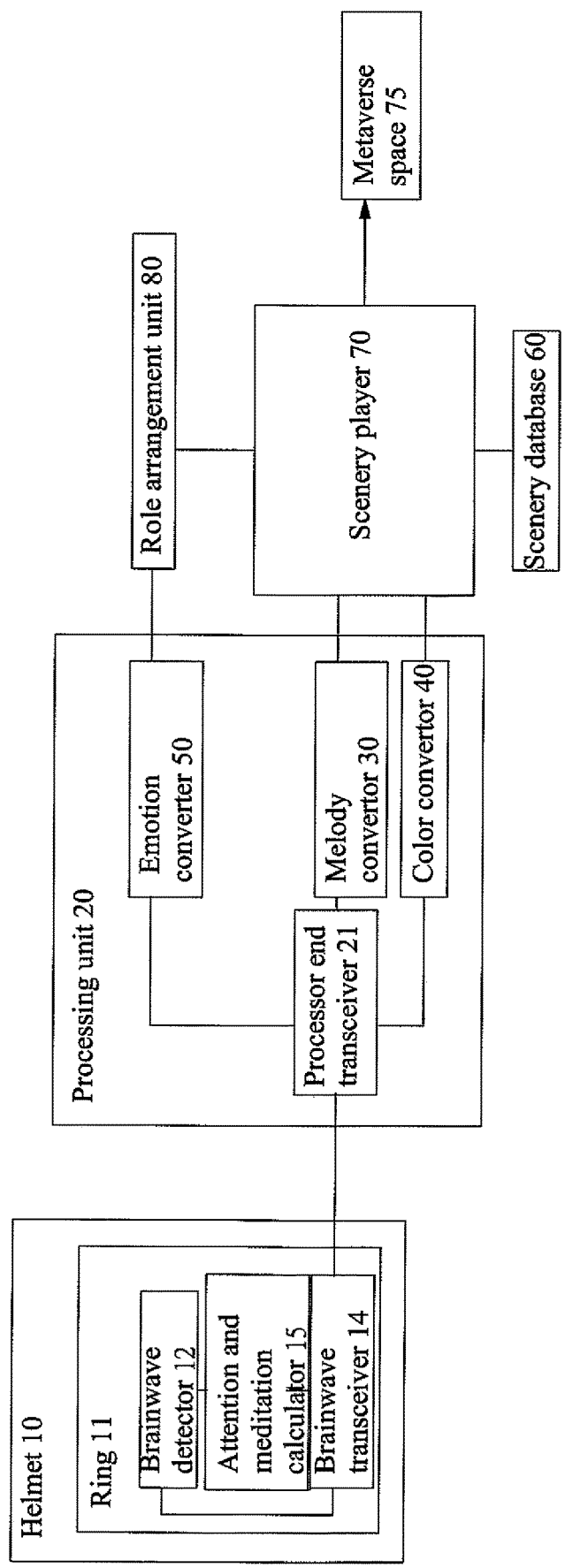
FIG. 1 is a functional block diagram of the elements of the present invention.
Figure 2:
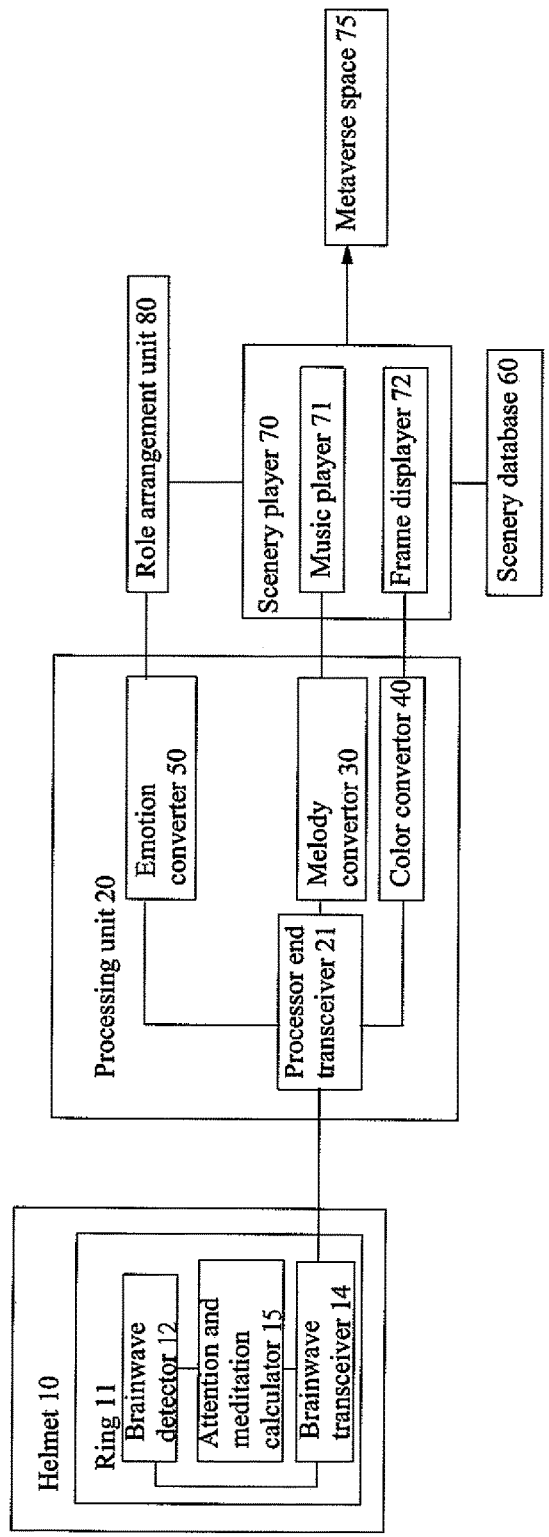
FIG. 2 is another functional block diagram of the elements of the present invention.
Figure 3:
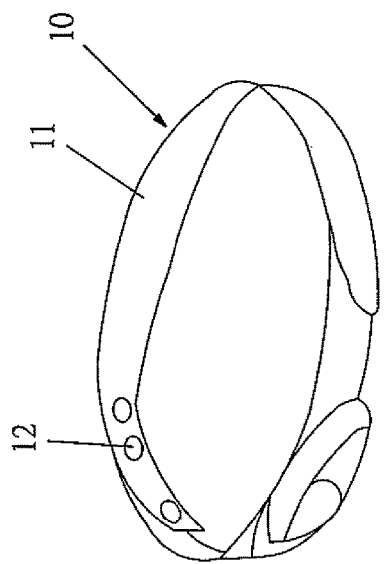
FIG. 3 is a schematic view showing the helmet of the present invention.
Figure 4:
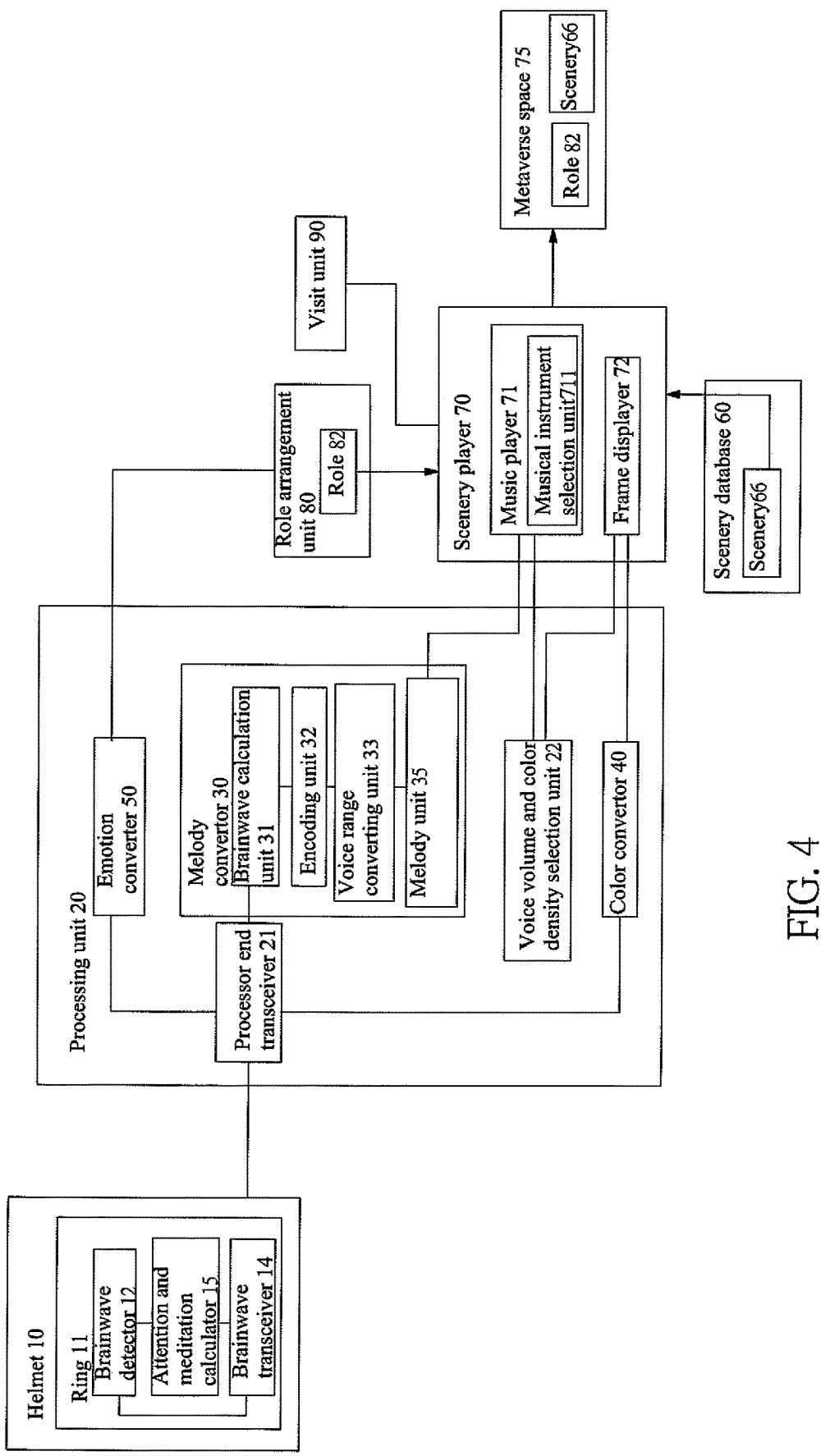
FIG. 4 is a schematic view showing the system of the present invention.
Figure 5:
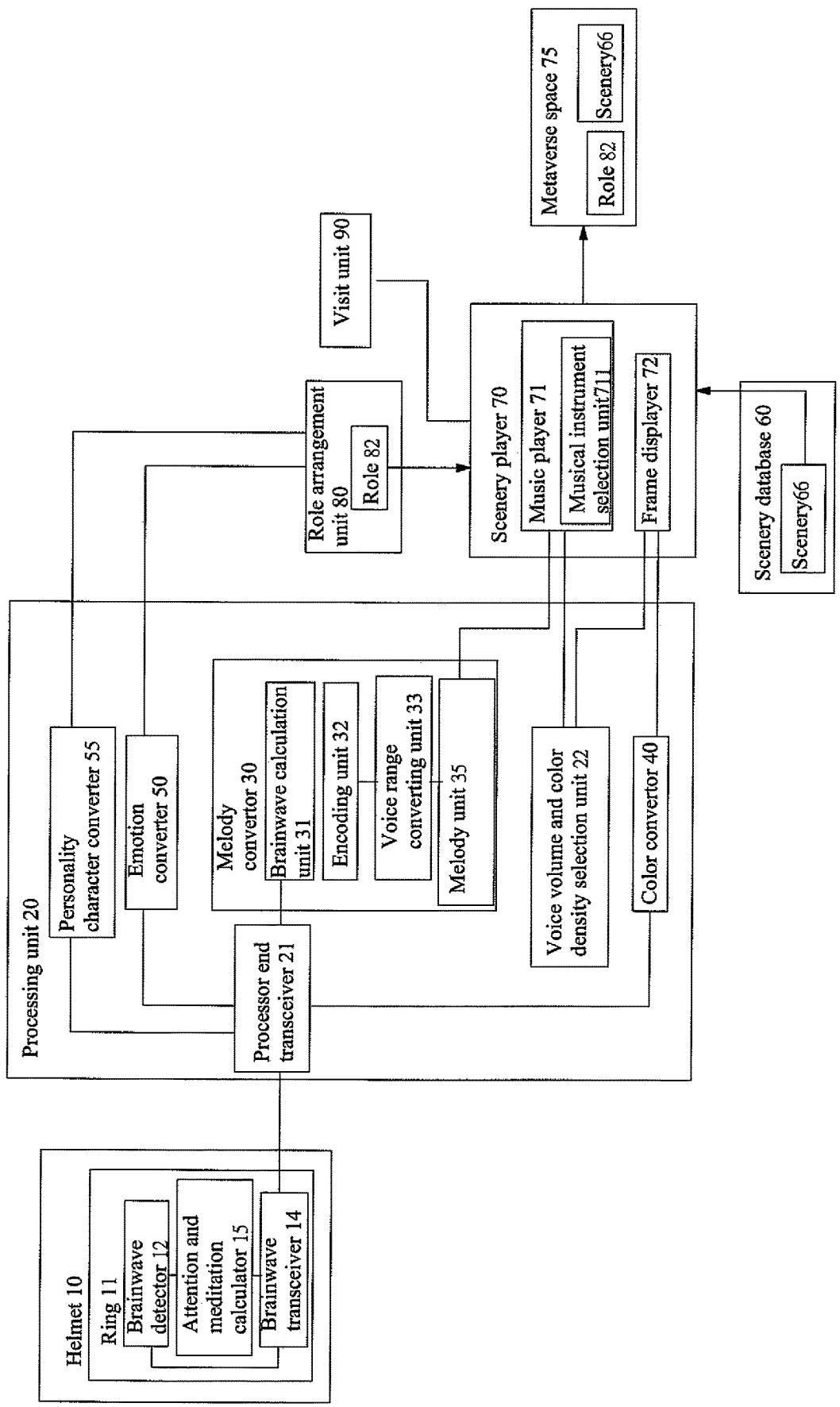
FIG. 5 is a block schematic view showing the personality character database of the present invention.
Figure 6:
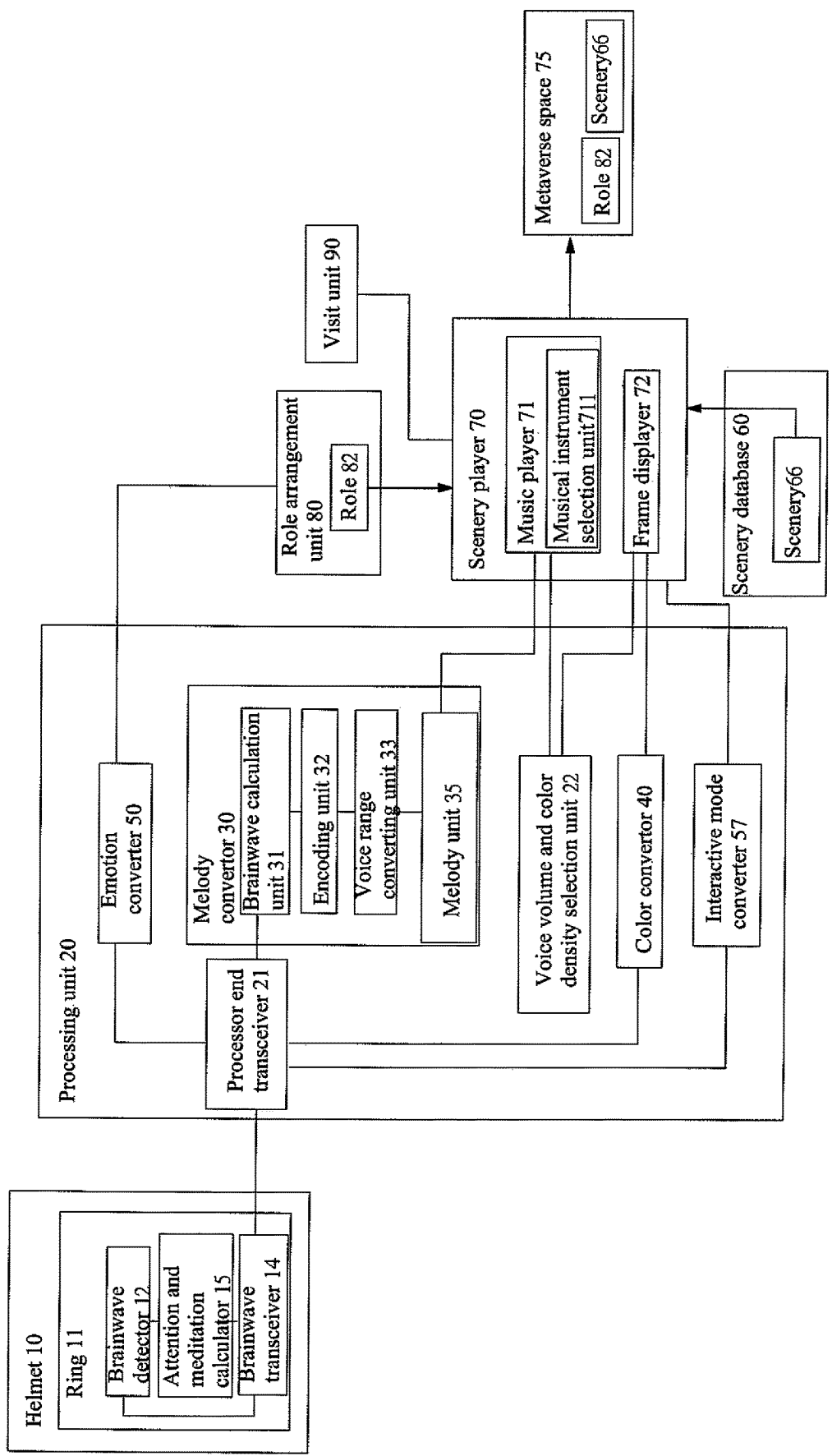
FIG. 6 is a block diagram showing the interactive mode converter of the present invention.

A helmet 10 serves to detect brainwaves of a user. In use, the helmet 10 is worn on the head of the user, as illustrated in FIGS. 1 and 2. The helmet 10 includes a ring 11, a brainwave detector 12 on the ring 11 for detecting brainwaves, and a detector transceiver 14 connected to the brainwave detector 12 for transmitting the brainwaves from the brainwave detector 12.

A processing unit 20 connected to the helmet 10 receives the brainwave signals from the helmet 10 and processing the signals. These brainwave signals includes signal of brainwaves from the left brain and right brain of the user, which contains Delta wave, Theta waves, High/Low Alpha waves, High/Low Beta waves and High/Low Gamma waves. The processing unit 20 may be installed in various electronic devices, such as computers, mobile phones, or tablet computers, etc.

The helmet 10 further includes an attention and meditation calculator 15 connected to the brainwave detector 12 for calculating the attention level and meditation level of the user by known algorithm (which is known in the prior art and thus the details will not be further described herein)

The processor 20 includes the following elements.

A processor end transceiver 21 is connected to the detector transceiver 14 of the helmet 10 for receiving signals from the brainwave transceiver 14.

A melody convertor 30 is connected to the processing end transceiver 21 for converting the brainwave signals of the user into respective music melodies by a specific algorithm, which is mainly based on the variations of Delta wave, Theta waves, High/Low Alpha waves, High/Low Beta waves and High/Low Gamma waves, and attention levels and meditation levels of the left and right brains of the user.

A color convertor 40 is connected to the processing end transceiver 21 for converting brainwave signals of the user into specific colors according to specific algorithms. For example, when the brainwaves show an anxiety state, a deep sink jitter color state is presented. When the brainwaves show that the user is in a low emotion state, grey like colors are presented.

An emotion converter 50 is connected to the processing end transceiver 21 for acquiring customer's emotions by received brainwaves.

A personality character converter 55 is connected to the processing end transceiver 21 for storing personality characters acquired from the brainwaves of users. Converting of personality characters being well known in the prior art and thus the details will not be described herein.

An interactive mode converter 57 is connected to the processing end transceiver 21 for analyzing interactive actions between the users and another visitor from the brainwaves thereof. The analyzing of the interactive actions between two persons is well known in the art and thus the details will not be further described herein.

A scenery database 60 stores various sceneries 66 which are selected by the users as a background space for presenting in a metaverse. The body of the user can be located in the selected scenery. The sceneries 66 is such as an indoor space, a garden, a factory, etc. Furthermore different sceneries are capable of being interconnected so that the users may, for example, walk out from an indoor space to a garden.

A scenery player 70 is connected to the scenery database 60 for displaying the music and melodies from the melody convertor 30, color messages from the color convertor 40, and the sceneries outputted from the scenery database 60. The states of the sceneries 66 will change based on the outputs from the melody convertor 30 and the color convertor 40.

A role arrangement unit 80 is connected to the scenery player 70 for arranging a role 82 selected by the user into the scenery 66 from the scenery player 70, wherein the scenery player 70 combines the role 82 and the scenery 66 into a metaverse space 75. The role 82, for example, may be a real person, a doll, an animal, a carton, etc. The role 82 may appear on the scenery, which represents the user himself (herself). The emotion converter 50 is connected to the role arrangement unit 80. The emotion converter 50 inputs the emotion of the user from the brainwaves to the role. When the user selects a role 82, the personality character converter 55 inputs the personality character to the role 82. The personality character may be static or time-dependent, i. e., dynamic.

By above mentioned structure, the user can select a scenery from the scenery database 60 which represents the space the user located in the metaverse. For example, the scenery may be an indoor space, which expresses that in the metaverse, the user is located in the indoor space and the scenery can be displayed to show that the user is in the indoor space.

In the present invention, the scenery 66 may be a 2 dimensional space or a 3 dimensional space, 3 dimensional space is preferably. Furthermore, if it is necessary that the scenery can be extended out, for example, an outer garden which is connected to the indoor space located the user, so when opening a door, the user may walk out to the garden. All these are selectable by the user.

The present invention further comprises a visit unit 90 which is connected to the scenery player 70. The visit unit 90 serves to receive visiting messages from visitors. These visiting messages can be presented on the scenery 66 of the user by the scenery player 70 so that both of the role 82 of the user and the visitor are able to be presented on the metaverse space of the user. When a visitor enters into the scenery 66 of the user, the interactive mode converter 57 will receive brainwaves of the visitor and then analyze interactions between the user and the visitor. The analyzed interaction will present to the user as reference.

By above mentioned way, a personal space can be presented on the metaverse space of the user. The helmet 10 will capture the brainwave signals and then these brainwave signals are converted into the music, color, emotions, and other data which are then present on the metaverse space 75. Hence, the metaverse space 75 shows the psychological state of the user.

The melody convertor 30 further comprises the following elements.

A brainwave calculation unit 31 serves to calculate brainwave strength difference between two adjacent time points for various brainwave parameters, wherein the brainwave parameter is selected from Att, Med, $\delta$, $\theta$, $\alpha-$, $\alpha+$, $\beta-$, $\beta+$, $\gamma-$, $\gamma+$, where the Att means the attention level, Med means the meditation level, and $\delta$ means Delta waves, $\theta$ means Theta waves, $\alpha-$ means Low Alpha waves, $\alpha+$ means High Alpha waves, $\beta-$ means Low Beta waves, $\beta+$ means High Beta waves, $\gamma-$ means Low Gamma waves, $\gamma+$ means High Gamma waves.

An encoding unit 32 is connected to the brainwave calculation unit 31, wherein the variations of the strength differences of the brainwaves in different time periods with respective to the brainwave parameters are encoded into respective coding values.

A voice range converting unit 33 is connected to the encoding unit 32. Based on values of the attention level and meditation level for each time period, by specific converting rules, the coding values are converted as respective notes, pitches, beats in that time period.

A melody unit 35 is connected to the voice range conversion unit 33 for arranging the notes of different time period converted from the voice range conversion unit 33 based on specific sequence so as to build music melodies in various time period. Then the melodies are outputted to the music player 71.

The scenery player 70 includes a music player 71 for playing the melody from, the melody unit 35 and a frame displayer 72 connected to the color convertor 40 for displaying colors from the color convertor 40. The melody convertor 71 could play music from the melody convertor 30 by MIDI formats.

The melody convertor 71 further includes a musical instrument selection unit 711 for selection of the musical instrument from the user and the timbre of the music instrument is used to play the melody determined above. Therefore, when there are a plurality of users, various music instruments are selected and combined to play the melodies from these users.

The color conversion unit 50 serves to map different sections of the brainwaves to different colors, wherein Delta wave is mapped to white color, Theta is mapped to red color, Low Alpha is mapped to orange color, High Alpha is mapped to yellow color, Low Beta is mapped to green color, High Beta is mapped to blue color, Low Gamma is mapped to indigo color, and High Gamma is mapped to purple color. When the music player 71 plays music, it transfers respective colors to the frame displayer 72 based on the brainwave sections corresponding to the notes.

The processing unit 20 further includes a voice volume and color density selection unit 22 which is connected to the music player 71 and the frame displayer 72. The amplitudes of the brainwaves in different time periods are divided into different sections which are mapped to different voice volumes and color densities for controlling the volume and color density of the music player 71 and the frame displayer 72.

Advantages of the present invention are that emotional messages, voice messages and color messages are captured from the brainwaves of the users. The emotional messages are integrated to the role of the user in the metaverse space. Hence, the role in the metaverse can respond the emotions of the user, while the voice messages and color messages are integrated into the sceneries in the metaverse, which is selected by the user. As a result, the metaverse space completely presents user's states of mind which are captured from the brainwaves of the users. Furthermore the whole sceneries and presentations of the roles in the metaverse space are adjustable with the changes of the users. It can also express user's personalities. Further, interaction modes between the users and visitors entering into the metaverse space of the user could be analyzed based on the method disclosed in the present invention. Therefore, the present invention cause that a social media could present a virtual reality which is lifelike and closer to the real life as the user live in a real world.

The present invention is thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A metaverse multimedia system based on brainwaves, comprising:
    a helmet for detecting brainwaves of a user; the helmet including a ring, a brainwave detector on the ring for detecting brainwaves, and a detector transceiver connected to the brainwave detector for transmitting the brainwaves from the brainwave detector;
    a processing unit connected to the helmet receiving the brainwave signals from the helmet and processing the signals; these brainwave signals including signals of brainwaves from the left brain and right brain of the user, which contains Delta wave, Theta waves, High/Low Alpha waves, High/Low Beta waves and High/Low Gamma waves;
    the processor including:
    a processor end transceiver connected to the detector transceiver for receiving signals from the brainwave transceiver;
    a melody convertor connected to the processing end transceiver for converting the brainwave signals of the user into respective music melodies by a specific algorithm;
    a color convertor connected to the processing end transceiver for converting brainwave signals of the user into specific colors according to specific algorithms;
    a scenery database storing various sceneries which are selected by the users as a background space for presenting in a metaverse;
    a scenery player connected to the scenery database for displaying the music and melodies from the melody convertor; color messages from the color convertor, and the sceneries outputted from the scenery database; the states of the sceneries changes based on the outputted from the melody convertor and the color convertor.

2. The metaverse multimedia system based on brainwaves as claimed in claim 1, further comprising a role arrangement unit connected to the scenery player for arranging a role selected by the user into the scenery from the scenery player, wherein the scenery player combines the role and the scenery into a metaverse space; the role appears on the scenery, which represents the user in the metaverse.

3. The metaverse multimedia system based on brainwaves as claimed in claim 2, further comprising an emotion converter connected to the processing end transceiver for acquiring emotions of the user from the brainwaves;
    wherein the emotion converter connected to the role arrangement unit for inputting the emotion to the role in the role arrangement unit so as to merge the emotion to the role selected on the role arrangement unit.

4. The metaverse multimedia system based on brainwaves as claimed in claim 2, wherein the role is selected from a real person, a doll, an animal, a carton.

5. The metaverse multimedia system based on brainwaves as claimed in claim 2, further comprising a visit unit is connected to the scenery player; the visit unit receiving visiting messages from visitors; these visiting messages can be presented on the scenery of the user by the scenery player so that both messages of the role of the user and the visitor are able to be presented on the metaverse space of the user.

6. The metaverse multimedia system based on brainwaves as claimed in claim 5, wherein the processing unit further comprises an interactive mode converter connected to the processing end transceiver for analyzing interactive actions between the users and another visitor from the brainwaves thereof; when a visitor enters into the scenery; the interactive mode converter receives the brainwaves of the visitor and then analyze the interaction modes between the user and the visitor which are then presented to the user as a reference.

7. The metaverse multimedia system based on brainwaves as claimed in claim 2, wherein the processing unit further comprises a personality character converter which is connected to the processing end transceiver for storing personality characters acquired from the brainwaves of users;
    wherein when a user selects a role, the personality character of the user is inputted to the role arrangement unit to be incorporated into the role selected so that the role selected can present the personality character;

wherein the personality character is changeable with the variation of the brainwaves of the user.

8. The metaverse multimedia system based on brainwaves as claimed in claim 1, wherein the scenery is a two dimensional or three dimensional space.

9. The metaverse multimedia system based on brainwaves as claimed in claim 1, further comprising an attention and meditation calculator connected to the brainwave detector for calculating the attention level and meditation level of the user, which are then inputted to the processing unit.

10. The metaverse multimedia system based on brainwaves as claimed in claim 9, further comprising a melody convertor connected to the processing end transceiver for converting the brainwave signals of the user into respective music melodies by a specific algorithm, which is mainly based on the variations of Delta wave, Theta waves, High/Low Alpha waves, High/Low Beta waves and High/Low Gamma waves, and attention levels and meditation levels of the left and right brains of the user.

11. The metaverse multimedia system based on brainwaves as claimed in claim 9, wherein the melody convertor further comprising;
- a brainwave calculation unit for calculating brainwave strength difference between two adjacent time points for various brainwave parameters, wherein the brainwave parameter is selected from Att, Med, $\delta$, $\theta$, $\alpha-$, $\alpha+$, $\beta-$, $\beta+$, $\gamma-$, $\gamma+$, where the Att means the attention level, Med means the meditation level, and $\delta$ means Delta waves, $\theta$ means Theta waves, $\alpha-$ means Low Alpha waves, $\alpha+$ means High Alpha waves, $\beta-$ means Low Beta waves, $\beta+$ means High Beta waves, $\gamma-$ means Low Gamma waves, $\gamma+$ means High Gamma waves;
- an encoding unit connected to the brainwave calculation unit, wherein the variations of the strength differences of the brainwaves in different time periods with respective to the brainwave parameters are encoded into respective coding values;
- a voice range converting unit connected to the encoding unit; based on values of the attention level and meditation level for each time period, by specific converting rules, the coding values are converted as respective notes, pitches, beats in that time period; and
- a melody unit connected to the voice range conversion unit for arranging the notes of different time period converted from the voice range conversion unit based on specific sequence so as to build music melodies in various time period; and then the melodies are outputted to the music player.

12. The metaverse multimedia system based on brainwaves as claimed in claim 1, wherein the scenery player includes a music player for playing the melody from the melody unit and a frame displayer connected to the color convertor for displaying colors from the color convertor.

13. The metaverse multimedia system based on brainwaves as claimed in claim 12, wherein the melody convertor further includes a musical instrument selection unit for selection of the musical instrument from the user and the timbre of the music instrument is used to play the melody.

14. The metaverse multimedia system based on brainwaves as claimed in claim 12, wherein the color conversion unit serves to map different sections of the brainwaves to different colors, wherein Delta wave is mapped to white color, Theta wave is mapped to red color, Low Alpha wave is mapped to orange color, High Alpha wave is mapped to yellow color, Low Beta wave is mapped to green color, High Beta wave is mapped to blue color, Low Gamma wave is mapped to indigo color, and High Gamma wave is mapped to purple color; when the music player plays music, it transfers respective colors to the display unit based on the brainwave sections corresponding to the notes.

15. The metaverse multimedia system based on brainwaves as claimed in claim 12, wherein the processing unit further includes a voice volume and color density selection unit which is connected to the music player and the frame displayer; amplitudes of the brainwaves in different time periods are divided into different sections which are mapped to different voice volumes and color densities for controlling the volume and color density of the music player and the frame displayer.

* * * * *